United States Patent [19]

Bryan

[11] Patent Number: 4,509,535
[45] Date of Patent: Apr. 9, 1985

[54] ELECTRODE APPARATUS

[76] Inventor: Horace Bryan, 12 Brighton 10 La., Brooklyn, N.Y. 11235

[21] Appl. No.: 385,531

[22] Filed: Jun. 7, 1982

[51] Int. Cl.³ .............................................. A61N 1/04
[52] U.S. Cl. .................................................... 128/798
[58] Field of Search ............... 128/783, 798, 799, 802, 128/803, 138 A, 384, 644

[56] References Cited

U.S. PATENT DOCUMENTS 3,386,445  6/1968  McDonald .......................... 128/798
3,759,246  9/1973  Flack et al. ................. 128/138 A X

FOREIGN PATENT DOCUMENTS 706582  6/1931  France ................................ 128/798
1541165  8/1968  France ................................ 128/384

Primary Examiner—Lee S. Cohen
Attorney, Agent, or Firm—Bernard Malina

[57] ABSTRACT

A device for relieving skin itch includes a flexible mesh sheet having a pair of spaced bare electrical wires interleaved within the sheet. An electrically non-conductive cover sheet is applied to one side of the mesh sheet while portions of the electrode wires are exposed on the other side of mesh sheet for contact application to the skin to relieve itching when a voltage is applied to the terminal ends of the electrode wires. The mesh sheet may be stored in a roll and cut to any desired length appropriate to the skin area to be treated.

10 Claims, 4 Drawing Figures

U.S. Patent  Apr. 9, 1985  4,509,535
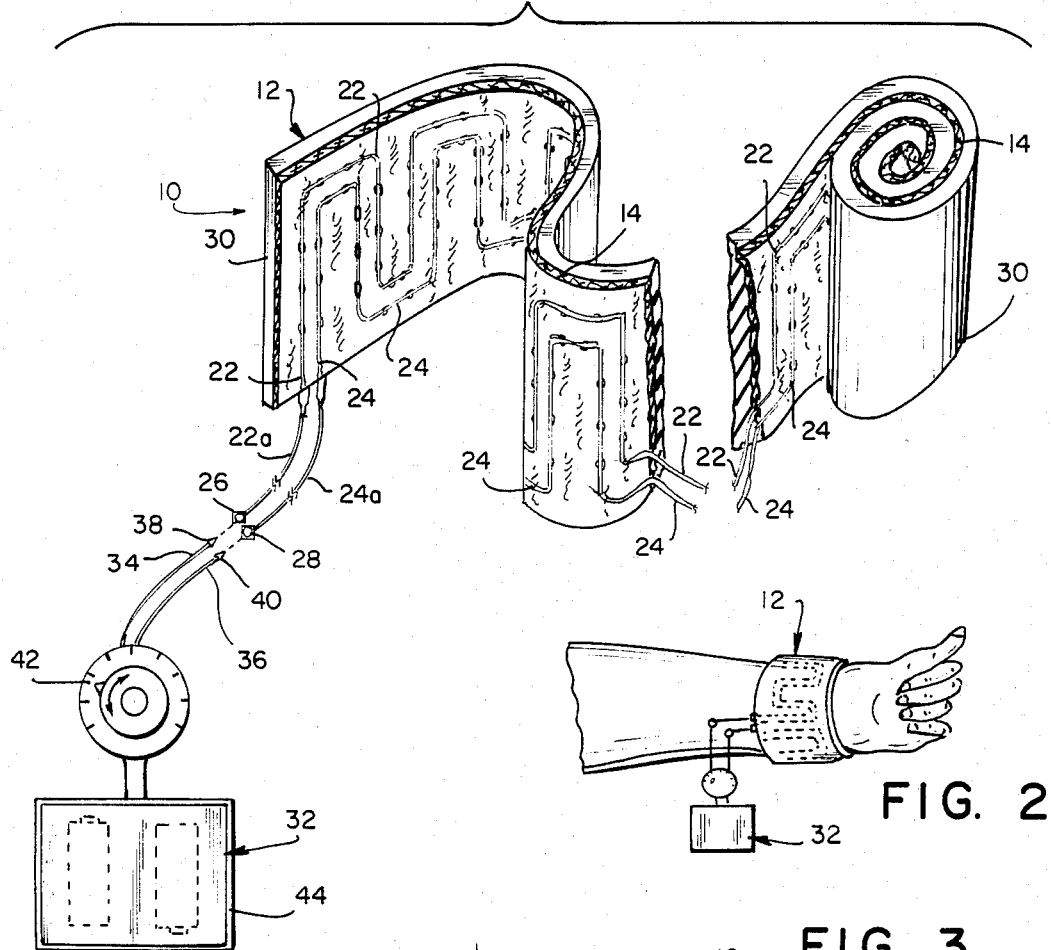
FIG. 1
FIG. 2
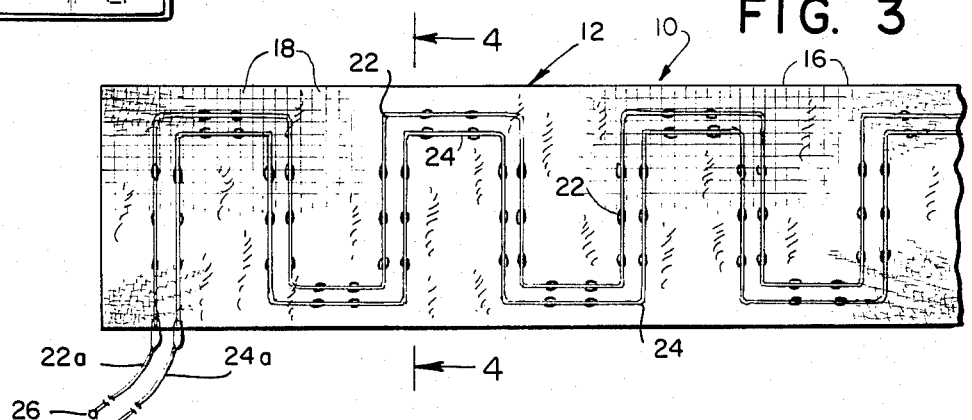
FIG. 3
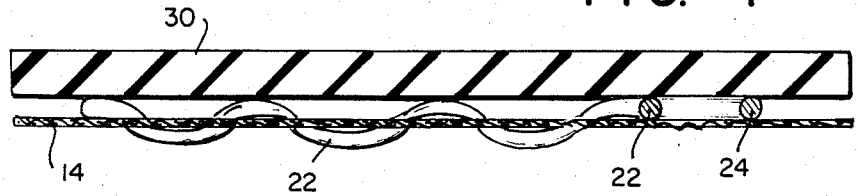
FIG. 4

ELECTRODE APPARATUS

BACKGROUND OF THE INVENTION

The present invention relates to apparatus for applying electrical stimulation to selected areas of the human body and more particularly to apparatus for applying electrically stimulating selected skin areas to counteract and relieve itching.

Itching sensations of skin areas of the human body often results from skin irritations produced by the application of bandages or plaster casts on injured limbs or other body areas, laceration or bruising of the skin, skin disorders, insect bites, etc. Scratching of the affected areas to relieve itching is generally not advised due to the danger of spreading the infection.

It is therefore an object of the present invention to provide an apparatus operative to provide electrical stimulation producing a mild stinging sensation to selected skin areas of the human body in order to provide itching relief thereon.

It is a further object of the present invention to provide an apparatus of the character described in which the magnitude of the electrical stimulation is selectively variable.

SUMMARY OF THE INVENTION

In accordance with the principles of the present invention, there is provided an electrode apparatus for contacting a human body comprising a planar flexible electrode assembly including a sheet of electrically non-conductive mesh-like material, a pair of flexible wire electrodes incorporated into said mesh sheet through the interstitial spaces thereof, a flexible planar cover sheet of electrically non-conductive material secured to one side of said mesh sheet and electrical terminal means connected to one of the terminal ends of each of said electrodes for selective connection thereof to a source of electrical power. The other side of said mesh sheet is adapted for contact application to a selected skin area of the human body.

Further objects, features and advantages of the invention will become apparent from a consideration of the following description, the appended claims and accompanying drawings in which:

BRIEF DESCRIPTION OF THE DRAWINGS

FIG. 1 is a perspective view in partial section of an apparatus in accordance with the principles of the present invention;

FIG. 2 is a perspective view of an application of the present invention;

FIG. 3 is a front elevation view of the electrode wrap of the apparatus of FIG. 1 in flat condition; and FIG. 4 is an enlarged section view taken along the line 4—4 of FIG. 3.

DETAILED DESCRIPTION OF THE INVENTION

With reference to the drawings, the apparatus of the present invention being generally designated by the numeral 10, comprises a flexible wrap 12 including a non-conductive mesh-like textile fabric 14 having grid spaced strands 18. A pair of parallel spaced fine electrical wire electrodes 22, 24 are woven into the fabric layer 14 through the interstitial spaces 16 thereof forming a wave-like pattern as shown in FIGS. 1 and 3.

The electrical input ends of electrodes 22 and 24 terminate respectively in a pair of input terminals 26, 28. The electrodes 22, 24 which are woven into the fabric layer 14 extending through the length thereof, are bare, i.e., not insulated, and are thus conductive on the surfaces along the entire lengths thereof. It is important to note that electrodes 22 and 24 are not in contact or joined at any point along their lengths in fabric layer 14.

An outer flexible solid electrically insulating cover layer 30 overlies gauze layer 14 which carries electrodes 22 and 24. Cover layer 30 may be made of any suitable flexible material such as plastic or fabric material, and extends over the entire upper surface of fabric layer 14 including the upper, but not lower surface areas of electrodes 22, 24.

Exposed electrodes 22 and 24 are closely woven into gauze-like layer 14 so as to provide adequate exposed electrode area protruding through the bottom surface of layer 14 for direct contact of said electrode areas with the skin areas in question. It should be noted, however, that electrode portions 22a and 24a which are not interwoven with gauze-like layer 14 are rigidly spaced apart and insulated to prevent short circuiting therebetween.

Flexible wrap 12 may be stored in roll form and cut to size for use as needed as shown in FIG. 1. Thus, in application, the user may apply wrap 12 to the selected skin area in a manner similar to the application of a bandage as illustrated in FIG. 2 by way of example. In applying wrap 12, gauze-like layer 14 with electrodes 22, 24 protruding therethrough is applied directly to the affected skin area and wrap 12 is secured to said area by any suitable means such as by means of tape applied to the outer cover layer 30.

An electrical power unit 32 may be connected to electrodes 22, 24 by any suitable means such as a pair of electrical leads 34, 36 provided with suitable connector terminals 38, 40 for releasably mating engagement with electrode terminals 26, 28. For portable applications, power unit 32 may be battery driven. Suitable controls 42 for selectively varying the magnitude and frequency and waveshape of the voltage produced on output leads 34, 36 may be located at a convenient position on the housing 44 of power unit 32.

In application, when wrap 12 is applied to the skin and electrical power is applied thereto by means of power unit 32 as described hereinabove, the selected skin area closes the electrical circuit between electrodes 22, 24, causing the selected electrical current to flow through electrodes 22, 24 and the selected skin areas. Thus, the various skin areas making electrical contact with both electrodes 22, 24 provide multiple parallel electrical loads across electrodes 22, 24.

As mentioned above, control 42 may be manipulated in order to produce a voltage having a selected magnitude, frequency and waveshape appropriate for the particular case, taking into account the condition, size and location of the skin area to which wrap 12 is to be applied. In many applications, pulsed voltage is advantageous to produce the desired itching relief. Thus, once wrap 12 has been applied to the skin area, the user may selectively vary the voltage output and/or vary the voltage frequency and/or waveshape until the desired relief is obtained. The stinging or tingling sensation produced by the electrical current serves to provide relief from itching. The user may maintain the application of electrical voltage to the affected skin area until he is satisfied with the adequacy of relief from itching.

While a preferred embodiment of the invention has been shown and described herein, it is obvious that numerous omissions, changes and additions may be made in such embodiment without departing from the spirit and scope of the invention.

What is claimed is:

1. An electrode apparatus for contacting a human body comprising: a planar flexible electrode assembly including a sheet of electrically non-conductive mesh-like material, first and second flexible electrically conductive wires incorporated into said mesh sheet along the length thereof in a spaced relationship through the interstitial spaces of said mesh sheet, a flexible planar cover sheet of electrically non-conductive material secured to one side of said mesh sheet, one of the terminal ends of each of said first and second wires being adaptable for selective connection to a source of electrical power at one end of the length of said mesh sheet, the other terminal ends of said first and second wires terminating at the other end of the length of said mesh sheet; the other side of said mesh sheet being adapted for contact application to a selected skin area of the human body.

2. An electrode apparatus as defined in claim 1 wherein at least a portion of the lengths of each of said electrically conductive wires protrudes through said other side of said mesh sheet for contact with said selected skin area when said mesh sheet is applied thereto.

3. An electrode apparatus as defined in claim 1 wherein said mesh sheet is flexible for conforming application to the contour of said selected skin area.

4. An electrode apparatus as defined in claim 3 wherein said mesh sheet is of textile material.

5. An electrode apparatus as defined in claim 1 wherein said one of the terminal ends of each of said first and second wires are located immediately adjacent one end of the length of said mesh sheet.

6. An electrode apparatus as defined in claim 1 wherein said one of the terminal ends of each of said first and second wires extend beyond said mesh sheet.

7. An electrode apparatus as defined in claim 1 wherein the portion of said wires incorporated into said mesh sheet are substantially parallel to each other in the plane of said mesh sheet.

8. An electrode apparatus as defined in claim 7 wherein said wires are of substantially wave shape configuration in the plane of said mesh sheet along the length of said mesh sheet.

9. An electrode apparatus as defined in claim 7 wherein said wires are closely spaced.

10. An electrode apparatus as defined in claim 1 wherein said mesh sheet is in strip-like configuration adaptable for storage in a rolled-up form whereby said mesh sheet incorporating said wires may be selectively cut to a suitable length.

* * * * *